United States Patent
Boersma et al.

(10) Patent No.: US 10,820,714 B2
(45) Date of Patent: Nov. 3, 2020

(54) TEMPERATURE-CONTROLLED MULTI-ZONE MATTRESS-STYLE SUPPORT

(75) Inventors: Joldert Maria Boersma, Zuidhorn (NL); Jacqueline Van Driel, Drachten (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 107 days.

(21) Appl. No.: 14/114,560

(22) PCT Filed: May 21, 2012

(86) PCT No.: PCT/IB2012/052532
§ 371 (c)(1),
(2), (4) Date: Oct. 29, 2013

(87) PCT Pub. No.: WO2012/160502
PCT Pub. Date: Nov. 29, 2012

(65) Prior Publication Data
US 2014/0109314 A1 Apr. 24, 2014

(30) Foreign Application Priority Data

May 23, 2011 (EP) .................... 11305633

(51) Int. Cl.
*A47C 21/04* (2006.01)
*A61F 7/00* (2006.01)
*A61F 7/02* (2006.01)

(52) U.S. Cl.
CPC .......... *A47C 21/044* (2013.01); *A47C 21/046* (2013.01); *A47C 21/048* (2013.01);
(Continued)

(58) Field of Classification Search
CPC ..... A47C 21/04; A47C 21/042; A47C 21/044; A47C 21/048; A47C 7/72; A47C 7/74; A47C 7/742; A47C 7/748
(Continued)

(56) References Cited

U.S. PATENT DOCUMENTS 718,896 A * 1/1903 Ames .......................... 607/112
723,797 A * 3/1903 Williams ..................... 607/108
(Continued)

FOREIGN PATENT DOCUMENTS

DE 102009010415 A1 9/2009
JP 10132435 A 5/1998
(Continued)

OTHER PUBLICATIONS

Raymann, Roy et al, "Diminished Capability to Recognize the Optimal Temperature for Sleep Initiation May Contribute to Poor Sleep in Elderly People", Sleep, 2008, Vol. 31, No. 9, pp. 1301-1309.
(Continued)

*Primary Examiner* — Peter M. Cuomo
*Assistant Examiner* — Ifeolu A Adeboyejo (57) ABSTRACT

A system for adjusting the microclimate of a bed environment includes a multi-zone mattress-style support having individual heating zones, a heater for heating the individual heating zones, a cooler for cooling the multi-zone mattress-style support, and temperature sensors. The cooler includes the multi-zone mattress-style support at least one air duct with the multi-zone mattress-style support for transporting ambient air through the multi-zone mattress-style support.

19 Claims, 3 Drawing Sheets

(52) U.S. Cl.
CPC ...... *A61F 7/007* (2013.01); *A61F 2007/0057* (2013.01); *A61F 2007/0065* (2013.01); *A61F 2007/0071* (2013.01); *A61F 2007/0298* (2013.01)

(58) Field of Classification Search
USPC .............. 5/421, 423, 652.1, 652.2, 724, 726
See application file for complete search history.

(56) References Cited

U.S. PATENT DOCUMENTS

| | | | | |
|---|---|---|---|---|
| 1,078,207 A * | 11/1913 | Michael | A61F 7/02 | 126/210 |
| 1,356,965 A * | 10/1920 | Charles | H05B 3/342 | 219/212 |
| 3,486,177 A * | 12/1969 | Marshack | A61G 7/057 | 5/726 |
| 3,529,310 A * | 9/1970 | Giuseppe | A47O 7/74 | 5/423 |
| 3,757,366 A * | 9/1973 | Sacher | A47C 21/044 | 5/423 |
| 3,859,506 A * | 1/1975 | Weckstein | H05B 3/56 | 219/529 |
| 4,114,620 A * | 9/1978 | Moore | A61F 7/02 | 5/421 |
| 4,132,262 A | 1/1979 | Wibell | | |
| 4,141,585 A * | 2/1979 | Blackman | 297/180.14 | |
| 4,162,393 A * | 7/1979 | Balboni | 219/217 | |
| 4,413,857 A * | 11/1983 | Hayashi | 297/180.11 | |
| 4,853,992 A * | 8/1989 | Yu | A47O 7/74 | 5/423 |
| 5,259,379 A * | 11/1993 | Kim | A47C 7/748 | 5/421 |
| 5,596,778 A * | 1/1997 | Suzuki | A47G 9/0215 | 5/423 |
| 5,835,983 A * | 11/1998 | McMahen | A61F 7/007 | 219/527 |
| 5,871,151 A * | 2/1999 | Fiedrich | A47C 21/048 | 237/69 |
| 5,882,349 A * | 3/1999 | Wilkerson | A47C 27/006 | 5/423 |
| 5,902,014 A * | 5/1999 | Dinkel | B60N 2/5635 | 297/180.1 |
| 5,934,748 A * | 8/1999 | Faust | B60N 2/5635 | 297/180.1 |
| 6,003,950 A * | 12/1999 | Larsson | A47O 7/74 | 297/180.13 |
| 6,006,524 A * | 12/1999 | Park | 62/3.7 | |
| 6,019,420 A * | 2/2000 | Faust | B60N 2/5635 | 297/180.12 |
| 6,186,592 B1 * | 2/2001 | Orizaris | B60N 2/5635 | 297/180.12 |
| 6,291,803 B1 * | 9/2001 | Fourrey | B60N 2/58 | 219/202 |
| 6,489,595 B1 * | 12/2002 | Check | B29C 65/02 | 219/202 |
| 6,519,964 B2 * | 2/2003 | Bieberich | A61F 7/0097 | 607/104 |
| 6,626,488 B2 * | 9/2003 | Pfahler | B60N 2/5635 | 297/180.11 |
| 6,676,207 B2 * | 1/2004 | Rauh | B60H 1/00285 | 297/180.14 |
| 6,687,937 B2 * | 2/2004 | Harker | 5/726 | |
| 6,786,541 B2 * | 9/2004 | Haupt | B60H 1/00285 | 297/180.1 |
| 6,808,230 B2 * | 10/2004 | Buss | B60N 2/5657 | 297/180.12 |
| 6,848,742 B1 * | 2/2005 | Aoki | B60N 2/5635 | 297/180.14 |
| 6,855,158 B2 | 2/2005 | Stolpmann | | |
| 6,969,827 B2 * | 11/2005 | Yoneyama | B60N 2/5685 | 219/202 |
| 7,040,710 B2 * | 5/2006 | White | B60N 2/5635 | 297/180.1 |
| 7,108,319 B2 * | 9/2006 | Hartwich | B60N 2/5635 | 297/180.1 |
| 7,134,715 B1 * | 11/2006 | Fristedt | B60N 2/002 | 177/144 |
| 7,178,357 B2 * | 2/2007 | Link | 62/440 | |
| 7,244,914 B2 * | 7/2007 | Yoneyama | H05B 3/34 | 219/202 |
| 7,261,371 B2 * | 8/2007 | Thunissen | B60N 2/56 | 297/180.14 |
| 7,555,792 B2 * | 7/2009 | Heaton | A61F 7/02 | 5/284 |
| 7,581,584 B2 * | 9/2009 | Yoneno | A47O 7/744 | 165/202 |
| 7,827,805 B2 * | 11/2010 | Comiskey | B60N 2/5635 | 62/244 |
| 7,942,477 B1 * | 5/2011 | Toba | B60N 2/002 | 297/180.12 |
| 8,777,320 B2 * | 7/2014 | Stoll | B60H 1/00285 | 297/180.1 |
| 8,888,573 B2 * | 11/2014 | Bajic | B60N 2/5635 | 297/180.1 |
| 2001/0020303 A1 | 9/2001 | Endo et al. | | |
| 2003/0046762 A1 | 3/2003 | Stolpmann | | |
| 2004/0069762 A1 * | 4/2004 | Yoneyama | B60N 2/5685 | 219/217 |
| 2006/0241730 A1 | 10/2006 | Huang | | |
| 2007/0251016 A1 * | 11/2007 | Feher | 5/713 | |
| 2008/0000025 A1 * | 1/2008 | Feher | 5/423 | |
| 2009/0064411 A1 | 3/2009 | Marquette | | |
| 2009/0099631 A1 | 4/2009 | Augustine et al. | | |
| 2010/0011502 A1 * | 1/2010 | Brykalski et al. | 5/423 | |
| 2010/0071130 A1 * | 3/2010 | Frias | A47C 21/044 | 5/421 |
| 2010/0100004 A1 | 4/2010 | Van Someren | | |
| 2010/0192299 A1 * | 8/2010 | Schermel | A47C 21/048 | 5/421 |
| 2010/0212088 A1 * | 8/2010 | Deighan | A47C 21/044 | 5/421 |
| 2010/0287701 A1 * | 11/2010 | Frias | A47C 21/044 | 5/423 |
| 2010/0325796 A1 * | 12/2010 | Lachenbruch | A61F 7/02 | 5/423 |
| 2011/0010850 A1 * | 1/2011 | Frias | A47C 21/048 | 5/423 |
| 2011/0041246 A1 | 2/2011 | Li et al. | | |
| 2012/0110734 A1 * | 5/2012 | An | A47C 21/048 | 5/423 |
| 2013/0205506 A1 * | 8/2013 | Lachenbruch | A47C 21/042 | 5/691 |
| 2013/0212808 A1 * | 8/2013 | Lachenbruch | A47C 27/05 | 5/691 |
| 2013/0298330 A1 * | 11/2013 | Lachenbruch | A61G 7/057 | 5/606 |
| 2014/0047646 A1 * | 2/2014 | Lachenbruch | A47C 21/044 | 5/726 |

FOREIGN PATENT DOCUMENTS

| | | |
|---|---|---|
| JP | 2001327551 | 11/2001 |
| JP | 2005007063 A | 1/2005 |
| WO | 9902074 A1 | 1/1999 |
| WO | 03022190 A2 | 3/2003 |
| WO | 2005120295 A1 | 12/2005 |
| WO | 2010044667 A1 | 4/2010 |

OTHER PUBLICATIONS

Raymann, Roy et al, "Skin deep: enhanced sleep depth by cutaneous temperature manipulation", Brain, (2008), vol. 131, pp. 500-513.

* cited by examiner

TEMPERATURE-CONTROLLED MULTI-ZONE MATTRESS-STYLE SUPPORT

CROSS-REFERENCE TO PRIOR APPLICATIONS

This application is the U.S. National Phase application under 35 U.S.C. § 371 of International Application No. PCT/IB2012/052532, filed on May 21, 2012, which claims the benefit of European Patent Application No. 11305633.7, filed on May 23, 2011. These applications are hereby incorporated by reference herein.

FIELD OF THE INVENTION

The invention relates to the field of apparatuses and methods for adjusting the temperature of a bed environment.

BACKGROUND OF THE INVENTION

Scientific studies have proven that the correct temperature in bed has a positive effect on a person's sleep. An independent study revealed significant improvements in sleep when the consumer's skin was slightly increased in temperature relative to the consumer's skin without temperature manipulation. Raymann et al., (Brain (2008), 131, 500-513) showed that subtle feedback control of in-bed temperature can have strong clinical relevance in the management of disturbed sleep especially for the elderly. Inducing a 0.4° C. increase in skin temperature of elderly subjects was sufficient to almost double the proportion of slow wave sleep and to decrease the probability of early morning awakenings from 0.58 to 0.04. A slight increase in bed temperature facilitates the initiation or reinitiation of sleep (Raymann et al., Sleep, Vol. 31, No. 9, pp.1301-1309, 2008).

The results of this study were obtained in that so-called "water pajamas" were used. These "water pajamas" are bodysuits having an impermeable inner layer and an impermeable outer layer, and water circulating between these two layers was kept constantly at a temperature of 35° C. However, such bodysuits are not consumer friendly devices and they are fairly expensive to manufacture.

Electrical blankets as a means for keeping a person warm and cozy are known for decades. The major disadvantage of such electric blankets is the fact that the temperature cannot be controlled in an appropriate manner. Usually a constant power input is applied and for some blankets the power settings can be changed in discrete steps. However, this does not take into account of any other conditions such as, for example, extra blankets on top of the bed, or the room temperature. Consequently, persons using electric blankets often complain about overheating during the night.

In addition, an electric blanket supplies the heat uniformly to the bed and does not distinguish between areas that do not have to be heated and areas that need more heating. Electric blankets having a separate heating zone for the feet of a person exist, but again they have a fixed heating power instead of a temperature control. Furthermore, qualitative and quantitative validation of using only a heating blanket offering constant temperature in bed has revealed that consumers also want a cooling functionality in such a device.

United States Patent Application Publication No. US 2010/0100004 A1 discloses skin temperature measurement in monitoring and control of sleep and alertness. Said publication teaches a method of influencing sleep by subtly manipulating the skin temperature of a sleeping person. It is stated that sleep can best be manipulated by controlling at least one of a proximal and distal skin area depending on the person concerned and the stage of sleep concerned. The method comprises controlling skin temperature in the subject such as to clamp the skin temperature 0.2 to 0.8° C. higher as compared to the skin temperature of the selected portion observed without or prior to manipulation, typically under normal sleeping circumstances. The thermal sleep treatment should preferably aim at individualized and time-of-night dependent control of skin temperature within predetermined ranges during sleep. For slight manipulation of sleep an arrangement is suggested comprising one or more temperature sensors and one or more temperature manipulating units, for instance in the form of one or more cooling elements and one or more heating elements. The temperature sensors may be implemented as a grid of miniature temperature sensors that are integrated in the bed beneath and/or above the sleeping person. The temperature control unit can be implemented in many different ways, for example with thermo-electric devices for heating and cooling, or by control of valves of a tubing system through which temperature-conditioned gas or liquid is circulated.

United States Patent U.S. Pat. No. 6,855,158 B2 teaches a thermo-regulating patient support structure comprising a plurality of air bladders defining a plurality of control zones, each of the plurality of air bladders having an air inlet and an air outlet, a plurality of temperature sensors, wherein at least one temperature sensor is coupled to each of the plurality of control zones, a circulator coupled to the air bladders and configured to move air from the air outlets to the air inlets, a temperature modulator coupled to the air bladders and configured to alter the temperature of air moved by the circulator, and a controller coupled to the circulator, the temperature modulator and the temperature sensors to control the temperature in each of the plurality of control zones based on the output signals from the temperature sensors.

Commercial products that offer both cooling and heating of a bed are available, for example under trade names AmbiSleep and Chillipad. The AmbiSleep device uses Peltier elements for heating or cooling air to levels below room temperature that is subsequently blown through a topper mattress. Chillipad uses water for heat transfer from a Peltier element in a base unit to a mattress topper which contains tubes for water circulation. The major drawback of these products is again that they only allow the user to set a specific heating or cooling power, and cannot control the temperature in bed while sleeping. Furthermore, the Peltier elements are not energy efficient, they are expensive, large and need fans for having its operation controlled which results in excessive noise. In most cases cooling of the air to below ambient temperature is not needed because the difference between the bed and the ambient temperature is large enough to get a cooling effect by the air flow in the bed.

SUMMARY OF THE INVENTION

It is a first object of the invention to provide a system for adjusting the microclimate of a bed environment to improve a person's sleep.

It is a further object of the invention to provide a method for adjusting the microclimate in a bed environment, and thereby improving a person's sleep.

In still another aspect, the invention pertains to the use of a system for adjusting the microclimate of a bed environment for improving a person's sleep.

The first object is achieved by a system that can heat and cool the bed environment based on the temperature which is measured in the bed and/or the sleeping room.

The second object is achieved by cooling and/or heating the bed environment based on the temperature which is measured in the bed environment and/or the sleeping room.

The third object is achieved by using a system that can heat and/or cool the bed environment based on the temperature which is measured in the bed and/or the sleeping room.

It is desirable to adjust the microclimate of a bed environment, in particular the temperature of a bed environment such that the sleep of a person sleeping within said bed environment is improved compared to a bed environment wherein the temperature is not adjusted. It is even more desirable that the microclimate of individual zones of the bed environment, in particular the temperature of said zones can be adjusted independently of each other.

A system according to an illustrative embodiment of the present invention comprises a multi-zone mattress-style support structure, a plurality of temperature sensors for monitoring the temperature of the bed environment in each zone of the mattress-style support structure, means for heating the individual zones of the mattress-style support structure, and means for cooling the mattress-style support structure.

The multi-zone mattress-style support may be implemented as a mattress which may be positioned directly on a slatted frame or a box spring. In another embodiment, the multi-zone mattress-style support may be implemented as a mattress topper that can be laid on top of a conventional mattress, for example between the current mattress of a person and the bedding. Preferably, the multi-zone mattress-style support is based on a polymer foam such as a polyurethane foam or a combination of different polymer foams, i.e. foam made of different polymers and/or foams which differ in properties such as density or elasticity, but being made of the same polymer. The multi-zone mattress-style support may also be configured as an inner spring mattress provided with a plurality of zones on at least one of its two faces.

The multi-zone mattress-style support includes a plurality of individual zones, the temperature of each zone of said plurality of individual zones can be adjusted separately by the heating means. The individual zones in which the temperature can be adjusted individually are designated as individual heating zones. The presence of individual heating zones allows to take into account the different temperatures of a sleeping person's torso and his or her extremities and adjust the bed environment accordingly.

The multi-zone mattress-style support further includes at least one duct for air, the at least one duct comprising an inlet opening and at least one outlet opening. In preferred embodiments, the multi-zone mattress-style support comprises a plurality of ducts, each duct comprising an inlet opening and at least one outlet opening, wherein the inlet openings of the ducts of the plurality of ducts may be joined to form a single inlet opening of the system. Alternatively or additionally, the outlet openings of the duct or the plurality of ducts, wherein each duct of the plurality of ducts comprises a single outlet opening, may be joined to form a single outlet opening of the system. In embodiments comprising two or more ducts, said ducts may be configured to provide individual zones which are designated cooling zones. The presence of individual cooling zones allows to account for the different temperatures of a sleeping person's torso and his or her extremities and adjust the bed environment accordingly.

In a preferred embodiment, one or more of the at least one air duct comprises a plurality of outlet openings, the outlet openings preferably being arranged to the side of the multi-zone mattress-style support preventing air to enter the bed and creating an air flow in the plane of the multi-zone mattress-style support. This embodiment is advantageous, because air flow might cool down the body of a sleeping person too fast, in particular if said person is sweating, and causes the person to wake up, and this embodiment prevents that air coming from the multi-zone mattress-style support will get in direct contact with the body of the sleeping person.

The heating zones of the multi-zone mattress-style support and the cooling zones of the multi-zone mattress-style support may be implemented as single individual zones, i.e., they are identical and cover the same surface area of the multi-zone mattress-style support. In alternative embodiments, the heating zones and the cooling zones are not identical zones, but they may overlap such that, for example, two or more heating zones cover a cooling zone.

The plurality of temperature sensors measure the temperature of the bed environment in their proximity. The plurality of temperature sensors is arranged such that each zone of the multi-zone mattress-style support includes at least one temperature sensor. This arrangement allows measuring the temperature of each of the individual zones of the multi-zone mattress-style support, preferably of the individual heating zones and/or the individual cooling zones. The temperature sensors are operatively connected to a controller for measuring the actual temperatures of the bed environment and for operating the heating means and/or cooling means.

In addition, the system may comprise at least one further temperature sensor which measures ambient air temperature in the sleeping room. Said at least one further temperature sensor is also operatively connected to a controller. The presence of at least one additional temperature sensor for measuring the ambient temperature allows consideration of the ambient temperature for adjusting the microclimate of the bed environment.

The heating means may be configured as a plurality of electrical resistance wires, wherein each of the individual heating zones includes at least one electrical resistance wire, the temperature of each of said at least one electrical resistance wires being controllable. The at least one electrical resistance wire of each individual heating zone is operable independently of the at least one electrical resistance wire of any other heating zone of the multi-zone mattress-style support. In an alternative embodiment, the heating means may comprise integrated heating yarns in a textile forming the upper portion of the multi-zone mattress-style support's envelope. Alternatively, the textile may form an individual layer underneath the upper portion of the multi-zone mattress-style support's envelope. Regardless of whether the textile, including the integrated heating yarn forms part of the multi-zone mattress-style support's envelope or an individual layer underneath the upper portion of the multi-zone mattress-style support's envelope, said textile is configured to form individual heating zones which can be heated individually.

In embodiments wherein the system is configured as a twin size (approx. 160 cm×200 cm), queen size (approx. 180 cm×200 cm) or king size (approx. 200 cm×200 cm) mattress or as a topper mattress fully covering the twin size, queen size or king size mattress, it is preferred that each half of the multi-zone mattress-style support in longitudinal direction comprises individual heating zones. Hence, the right half of the multi-zone mattress-style support includes a plurality of individual heating zones, and the left half of the multi-zone mattress-style support comprises a plurality of individual heating zones. This configuration has the advantage that the bed environment, in particular the heating, can be individually adjusted for two individuals sleeping in the same bed at the same time.

The cooling means comprise at least one air duct within the multi-zone mattress-style support. In one embodiment, the cooling means comprises a single air duct, said air duct extends under substantially the entire upper surface area of the multi-zone mattress-style support. In alternative embodiments, the cooling means comprise a plurality of air ducts, said plurality of air ducts extending under substantially the entire upper surface area of the multi-zone mattress-style support.

In an additional alternative embodiment, the cooling means comprising a plurality of air ducts is configured to form individual cooling zones. When the system is configured as a twin size (approx. 160 cm×200 cm), queen size (approx. 180 cm×200 cm) or king size (approx. 200 cm×200 cm) mattress or as a topper mattress fully covering the twin size, queen size or king size mattress, it is preferred that the cooling means comprises at least two cooling zones, a first cooling zone and a second cooling zone, wherein each of the cooling zones represents one half of the multi-zone mattress-style support in a longitudinal direction. Hence, the first cooling zone represents the right half of the multi-zone mattress-style support, and the second cooling zone represents the left half of the multi-zone mattress-style support. This configuration has the advantage for the bed environment, in particular the cooling, can be individually adjusted for two individuals sleeping in the same bed at the same time.

The cooling means may further comprise at least one fan for blowing air into or sucking air out of the air duct(s). The at least one fan is preferably arranged in the system such that no air can escape from the exit of the fan before entering the at least one air duct. For example, the at least one fan can be arranged within an air duct or in an aspiration port for a plurality of air ducts. The at least one fan is configured such that its operation does not cause noise which would impair a person's sleep when sleeping in close vicinity of the at least one fan. The at least one fan may be located at the head end or at the foot end of the multi-zone mattress-style support. In case of a plurality of fans, all fans may either be located at the same end or the same side of the multi-zone mattress-style support. Alternatively, the fans or the plurality of fans may be located at multiple end or sides of the multi-zone mattress-style support. The at least one fan transports ambient air into the air duct(s). The ambient air is not actively cooled (i.e., cooled to a level below bed room temperature) before being provided to the air duct(s). Usually the ambient air has a lower temperature than the bed environment underneath a sleeping person's blanket. Therefore, cooling the bed environment is considered as "passive cooling". The at least one fan is operatively connected to a controller.

In another embodiment, the cooling means comprises means for lowering the temperature of the air that will be blown through the at least one air duct below ambient temperature, i.e. below the bed room temperature. This type of cooling is considered as "active cooling". The means for lowering the air below ambient temperature may be selected from the group consisting of Peltier elements and cooling compressor units. This embodiment has the advantage, that the microclimate of the bed environment can be adjusted within a larger range of temperatures compared to passive cooling. The at least one means for lowering the temperature of the air that will be blown through the at least one air duct below ambient temperature is operatively connected to a controller. In the embodiment, at least one fan is present which forces the air being subject matter to active cooling through the at least one air duct.

The heating means and the cooling means are separate means, i.e., the heating means are not configured to be the cooling means too, and vice versa.

The plurality of electrical resistance wires or the plurality of textiles comprising integrated heating yarns of the heating means, and the air ducts of the cooling means can be integrated into the multi-zone mattress-style support in several ways. In an embodiment, the electrical resistance wires are located in a layer on top of a layer comprising the air ducts. The top layer including the electrical resistance wires is made of an open structure such that the cooling air can pass through said top layer. In an alternative embodiment, the air cooling layer is placed on top of the layer comprising the electrical resistance wires. In this embodiment, the top layer is configures such that the air can transport the heat which is generated in the layer beneath to the top surface of the multi-zone mattress-style support. In still another embodiment, the multi-zone mattress-style support comprises a first face having the heating zones as a layer underneath the surface of this face, and a second face on the opposite side of the first face, said second face having the cooling zones as a layer underneath the surface of this second face. This embodiment allows the user to have the cooling side on top in the summer time, and to turn the multi-zone mattress-style support upside down such that the heating side is on top in the winter time.

In another embodiment, the air flow is in contact with the electrical resistance wires. This way the air can be heated in the topper to assist in the heat transfer into the bed. Also this way, the amount of moisture that can be taken up in the air flow through the topper can be increased which will help in drying the bed and removal of body fluids (sweat) from the bed environment.

The system further comprises a controller for receiving the signals from the plurality of temperature sensors, and operating the heating means and the at least one fan of the cooling means. Said controller may be configured to switch-off the heating when a maximum temperature is reached. Thereby additional safety is provided for the user of the system, i.e., the sleeping person.

The system of the present invention permits to adjust the microclimate of a bed environment while a person is sleeping in the bed, and to provide optimal temperature for an improved sleep taking into account the temperature of the bed environment in separate zones, optionally the ambient temperature in the sleeping room, and to increase or reduce the temperature in individual zones of the bed environment.

The system as described herein above can be used to adjust the microclimate of a bed environment. Adjusting the microclimate of a bed environment can improve the sleep of persons when sleeping in the adjusted microclimate compared to sleeping in a non-adjusted microclimate. According to a preferred embodiment, the system of the present invention can be used to adjust the microclimate of a bed environment to a temperature of between 26° C. and 36° C., which turns out to be the optimal temperature range for improving a person's sleep. In an additional embodiment, the system can be used to pre-warm the bed such that the comfort is increased when a person enters the bed for sleeping. In another or additional embodiment, the system can be used to set different temperatures for the time between entering the bed and the time falling asleep, after which the control of the microclimate takes over. In the morning, the system can also be used to change the temperature of the bed environment for waking up the sleeping person.

The present invention also provides a method for adjusting the microclimate of a bed environment for improving a person's sleep, and a method for improving a person's sleep by adjusting the microclimate of the bed environment said person is sleeping in.

The methods comprise measuring the temperature of the bed environment in individual zones, and adjusting the temperature of the bed environment in the individual zones such that the temperature in said individual zones is kept at a preferred, preset temperature. The temperatures of the individual zones are adjusted in that the individual zones are warmed or cooled to the preset temperature. Said preset temperature is preferably in a range of between 26° C. and 36° C. Warming is performed in that at least one electrical resistance wire in each individual heating zone is subjected to an electric current thereby becoming warm. The warmth is conducted from the electrical resistance wire through the layer or layers between said electrical resistance wire and the upper face of a multi-zone mattress-style support by conduction. The chill is provided in that air is forced to flow through at least one air duct within the multi-zone mattress-style support. If the air flow is combined with heating at the same time, moisture removal from the bed will be increased due to the diffusion of moisture through the topper into the warm air. Also heat exchange with the person in bed will be increased due to convection.

The ambient air may be the air of the sleeping room where the multi-zone mattress-style support is placed. However, the ambient air may be obtained from an environment outside the sleeping room where the multi-zone mattress-style support is placed, for example, air from outside a building that can be acquired via a pipe or tube.

In an embodiment of the method, the temperature of the air that is forced through the at least one air duct within the multi-zone mattress-style support is not lowered below the temperature of the ambient air, i. e. the temperature of the air in the bed room. Forcing air through the at least one air duct within the multi-zone mattress-style support, wherein the temperature of the air that is forced through the at least one air duct in not lowered below ambient air temperature, can be performed by using one or more fans.

In an alternative embodiment of the method, the temperature of the air that will be forced through the at least one air duct within the multi-zone mattress-style support is lowered below the temperature of the ambient air, i. e. the temperature of the air in the bed room. The temperature of the air which shall be forced through the at least one air duct can be lowered below ambient air temperature by means which are for example selected from the group consisting of Peltier elements and cooling compressor units. This embodiment of the method further utilizes at least on fan for forcing the air having a temperature below ambient air temperature through the at least one air duct.

The present invention further extends to the use of the system for adjusting the microclimate of a bed environment. More specifically, the invention extends the use of the system for controlling the moisture in the bed environment. In particular, using heating by means of electrical resistance wires in combination with air flow enhances and improves control of moisture in the bed environment. Hence, the present invention also comprises a method for controlling the moisture in a bed, the method comprises using a combination of heating the bed environment by means of electrical resistance wires, and providing an air flow in the bed environment. As the human body loses 0.25 to 0.5 litre each night, controlling the moisture in the bed environment will extend the lifetime of the mattress and also improve the hygiene in the bed. Changing temperature of air will allow the air to take up more moisture (humidity). This will result in a higher flux of water out of the bed into the flowing air.

BRIEF DESCRIPTION OF THE DRAWINGS

These and other aspects of the invention will be apparent from and elucidated with reference to the embodiments described hereinafter.

In the drawings.

DETAILED DESCRIPTION OF EMBODIMENTS

Figure 1A:
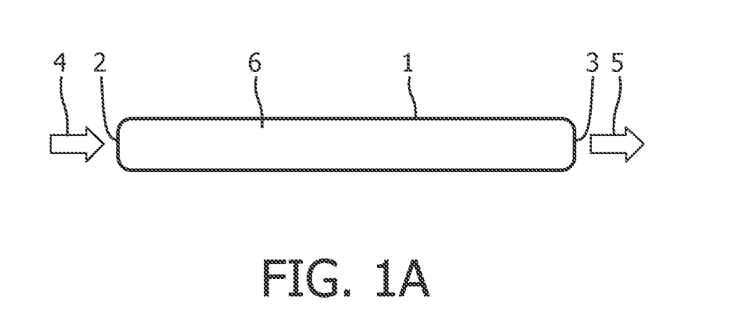
FIG. 1A shows a schematic longitudinal section of and illustrates the air flow through one embodiment of the system for adjusting the microclimate in a bed environment.

FIG. 1A shows a schematic representation of an embodiment of the multi-zone mattress-style support 1 in a longitudinal section. In one embodiment, the multi-zone mattress-style support 1 may be implemented as a topper mattress fully covering a mattress 10 shown in dashed lines. The multi-zone mattress-style support 1 comprises an inlet opening 2 and an outlet opening 3 of an air duct 6. The inlet opening 2 and the outlet opening 3 are positioned at opposite ends of the multi-zone mattress-style support 1. Arrow 4 indicates the flow direction of air entering the air duct 6 at its inlet opening 2, whereas arrow 5 indicates the flow direction of the air leaving the air duct 6 at its outlet opening 3. In this embodiment, the air is transported unidirectional through the air duct 6 within the multi-zone mattress-style support 1. The air is ambient air and cools the multi-zone mattress-style support 1 when its temperature is lower than the temperature of the bed environment above the multi-zone mattress-style support 1.

Figure 1B:
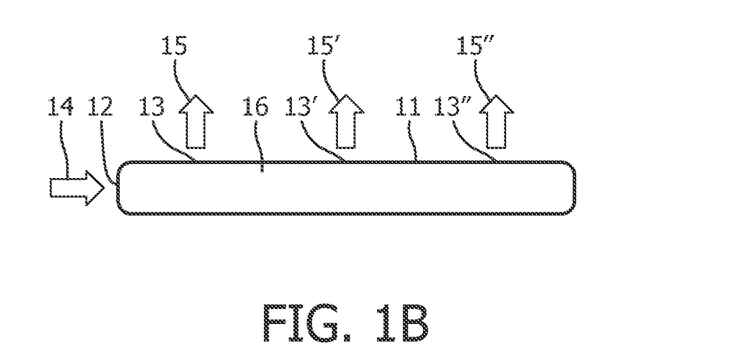
FIG. 1B shows a schematic longitudinal section of and illustrates the air flow through another embodiment of the system for adjusting the microclimate in a bed environment.

FIG. 1B shows a schematic representation of another embodiment of the multi-zone mattress-style support in a longitudinal section. The multi-zone mattress-style support 11 comprises an inlet opening 12, an air duct 16 and a plurality of outlet openings 13, 13' and 13" at the top face of the multi-zone mattress-style support 11. When ambient air enters the multi-zone mattress-style support 11 via inlet opening 12 as indicated by arrow 14, and is transported through air duct section 16 to exit said air duct 16 at the plurality of outlet openings 13, 13' and 13". The cooling can be improved in that the ambient air is blown through the upper face of the multi-zone mattress-style support 11. Moreover, cooling can be focused on individual zones, namely on zones comprising at least one outlet opening of the plurality of outlet openings 13, 13' and 13".

Figure 2A:
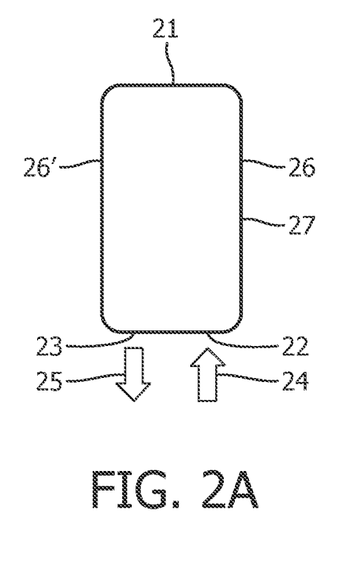
FIG. 2A shows a schematic top view of and illustrates the air flow through one embodiment of the system for adjusting the microclimate in a bed environment.

Referring to FIGS. 2A to 2D, different embodiments of multi-zone mattress-style supports are shown in elevated views which illustrate various implementations of air ducts and/or zones. FIG. 2A shows a multi-zone mattress-style support 21 comprising an inlet opening 22 at a first end of an air duct section 26, and an outlet opening 23 at the other end of the air duct section 26, 26', wherein said inlet opening 22 and said outlet opening 23 are located at the same end of the multi-zone mattress-style support 21. Hence, the air duct section 26, 26' is configured to make a U-turn and a first portion 26 of the air duct section is separated from a second portion 26' of the air duct section by a separating wall 27. Hence, ambient air can enter the multi-zone mattress-style support 21 in that it is blown into the air duct section 26, 26' through inlet opening 22 as indicated by arrow 24. The air is blown through the first portion 26 and the second portion 26' of the air duct section 26, 26' to exit the multi-zone mattress-style support 21 through outlet opening 23 as indicated by arrow 25.

Figure 2B:
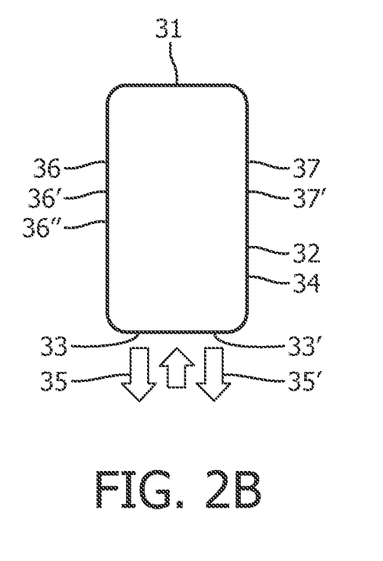
FIG. 2B shows a schematic top view of and illustrates the air flow through another embodiment of the system for adjusting the microclimate in a bed environment.

FIG. 2B represents another embodiment of the multi-zone mattress-style support, wherein the multi-zone mattress-style support 31 comprises an air duct section 36, 36', 36", an inlet opening 32 and two outlet openings, a first outlet opening 33 and a second outlet opening 33'. The inlet opening 32, the first outlet opening 33 and the second outlet opening 33' are located at the same end of the multi-zone mattress-style support 31. The air duct section comprises a first portion 36, a second portion 36' and a third portion 36", wherein the second portion 36' and the third portion 36" of the air duct section result from a bifurcation of the first portion 36 of the air duct section such that the flow direction in the second portion 36' and the third portion 36" of the air duct section is opposed to the flow direction in the first portion 36. The first portion 36 of the air duct section is separated from the second portion 36' of the air duct section by a first separating wall 37, and is separated from the third portion 36" by a second separating wall 37'. Hence, the first portion 36 of the air duct section is flanked by the second portion 36' and the third portion 36" of the air duct section. Ambient air is forced to enter the first portion 36 of the air duct section via inlet opening 32 as represented by arrow 34. The air migrates to the end of the multi-zone mattress-style support 31 which is opposite the inlet opening 32 and the outlet openings 33 and 33', and then migrates back to the end of the multi-zone mattress-style support 31 where the inlet opening 32 and the outlet openings 33 and 33' are located. This embodiment has the advantage that the medial section of multi-zone mattress-style support 31 corresponding to the first portion 36 of the air duct section is provided with cooler air than the flanking sections of the multi-zone mattress-style support 31 which correspond to the second portion 36' and the third portion 36" of the air duct section respectively. Usually the torso of a sleeping person is located in the medial section of a mattress, and the arms and legs are lying next to the torso in regions corresponding to the flanking sections of the multi-zone mattress-style support 31.

Figure 2C:
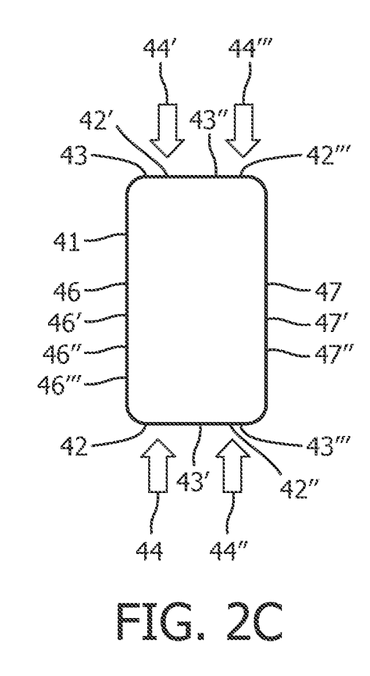
FIG. 2C shows a schematic top view of and illustrates the air flow through another embodiment of the system for adjusting the microclimate in a bed environment.

FIG. 2C represents still another embodiment of the multi-zone mattress-style support. The multi-zone mattress-style support 41 comprises a plurality of air duct sections 46, 46', 46", 46''' which proceed unidirectional in a longitudinal direction of the multi-zone mattress-style support 41 and are positioned essentially parallel to each other. The air ducts are separated from each other by individual separating walls 47, 47', 47". Each air duct section 46, 46', 46", 46''' has an inlet opening 42, 42', 42", 42''' at one end and an outlet opening 43, 43', 43", 43''' at its opposite end. Ambient air is blown into each of the plurality of air duct sections 46, 46', 46", 46''' through the respective inlet opening 42, 42', 42", 42''' and leaves the air duct sections 46, 46', 46", 46''' at the respective outlet opening 43, 43', 43", 43'''. The ambient air may be supplied to all the air duct sections 46, 46', 46", 46''' at one end of the multi-zone mattress-style support 41, or as indicated by arrows 44, 44', 44", 44''' such that the flow direction of the air through the multi-zone mattress-style support 41 occurs in opposite directions with respect to neighboring air ducts.

Figure 2D:
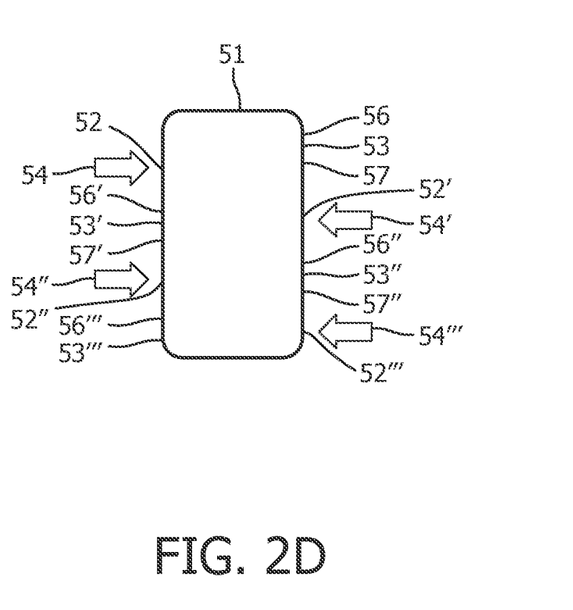
FIG. 2D shows a schematic top view of and illustrates the air flow through another embodiment of the system for adjusting the microclimate in a bed environment.

Yet another embodiment of the multi-zone mattress-style support is shown in FIG. 2D. The multi-zone mattress-style support 51 comprises a plurality of air duct sections 56, 56', 56", 56''' which proceed unidirectional in a lateral direction of the multi-zone mattress-style support 51, which is perpendicular to a longitudinal axis of the multi-zone mattress-style support, and which are positioned essentially parallel to each other. The air ducts are separated from each other by individual separating walls 57, 57', 57". Each air duct section 56, 56', 56", 56''' has an inlet opening 52, 52', 52", 52''' at one end and an outlet opening 53, 53', 53", 53''' at its opposite end. Ambient air is blown into each of the plurality of air duct sections 56, 56', 56", 56''' through the respective inlet opening 52, 52', 52", 52''' and leaves the air duct sections 56, 56', 56", 56''' at the respective outlet opening 53, 53', 53", 53'''. The ambient air may be supplied to all the air duct sections 56, 56', 56", 56''' at one end of the multi-zone mattress-style support 51, or as indicated by arrows 54, 54', 54", 54''' such that the flow direction of the air through the multi-zone mattress-style support 51 occurs in opposite directions with respect to neighboring air ducts. Instead of proceeding from the head end to the foot end of a multi-zone mattress-style support as is shown in FIG. 2C, the air ducts proceed from the left side of the multi-zone mattress-style support 51 to the right side of the multi-zone mattress-style support 51.

Each of the air duct sections shown in any one of FIGS. 2A to 2D may comprise at least one air duct. Preferably, each of these air duct sections comprises a plurality of air ducts proceeding essentially parallel to each other. Each of the air duct sections shown in FIGS. 2A to 2C may represent at least one cooling zone or a plurality of individual cooling zones. In addition, each of the air duct sections shown in FIGS. 2A to 2C may also correspond to at least one heating zone or a plurality of individual heating zones. For example, with reference to FIG. 2D, air duct section 56 representing the air duct section at the head end of the multi-zone mattress-style support 51 may represent a first heating zone of said multi-zone mattress-style support 51. The air duct section 56' may also represent another heating zone of the multi-zone mattress-style support 51. It is to be understood that each of the air duct sections may also represent a plurality of individual heating zones.

Figure 3:
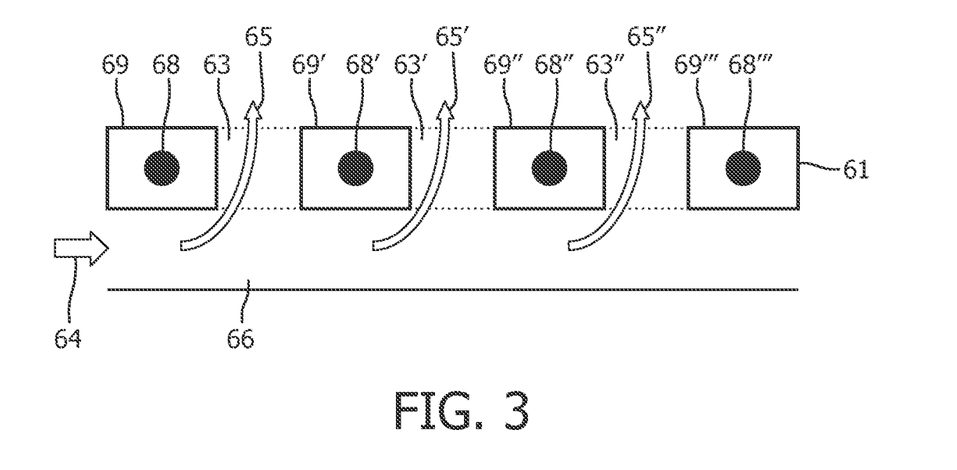
FIG. 3 is a more detailed representation of a longitudinal section of an embodiment of the system for adjusting the microclimate in a bed environment.
Figure 4:
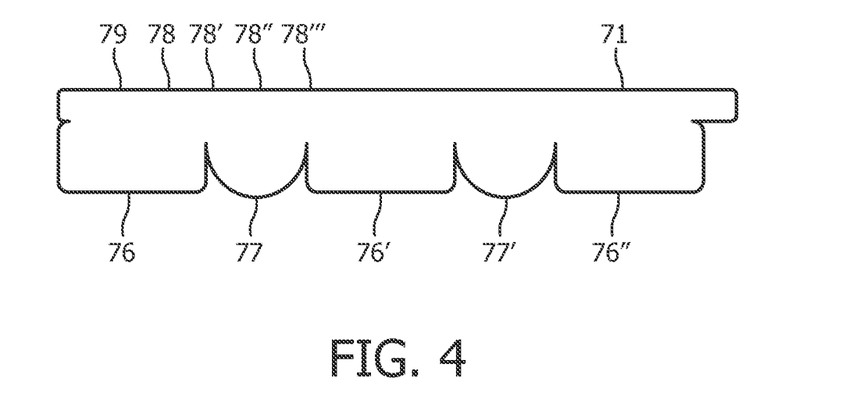
FIG. 4 is a more detailed representation of a longitudinal section of another embodiment of the system for adjusting the microclimate in a bed environment.

With reference to FIGS. 3 and 4 suitable assemblies of the multi-zone mattress-style support are illustrated. FIG. 3 displays a portion of a multi-zone mattress-style support 61 in a longitudinal section. The multi-zone mattress-style support 61 comprises an air duct 66 and a layer on top of the air duct 66. The layer on top of the air duct 66 is preferably a layer made of an elastic polymer foam and comprises a plurality of outlet openings 63, 63' and 63" within a polymer foam which is separated into sections 69, 69', 69" and 69'". Each of the sections 69, 69', 69" and 69'" comprises an electrical resistance wire 68, 68', 68" and 68'", wherein the electrical resistance wires proceed perpendicular to the air duct 66. It is to be understood that one or more additional layers may placed on top of the layer comprising the sections 69, 69', 69" and 69'" and the outlet openings 63, 63' and 63". Said at least one additional layer may be a thin layer of an elastic polymer foam or a woven textile.

Upon heating, the electrical resistance wires are subjected to an electrical current and become warm. The warmth will migrate through the polymer foam to the top of the multi-zone mattress-style support 61 and warm up the bed environment until a preset temperature is achieved. When the bed environment is to be cooled, ambient air is blown into the air duct 66 as indicated by arrow 64. The air flowing through air duct 66 will leave the multi-zone mattress-style support 61 through the plurality of outlet openings 63, 63' and 63" as indicated by arrows 65, 65' and 65" thereby reducing the temperature of the bed environment.

FIG. 4 illustrates another embodiment of assembling the multi-zone mattress-style support. The multi-zone mattress-style support 71 comprises a plurality of air ducts 76, 76' and 76" which are separated from each other by separating walls 77 and 77'. The separating wall 77 and 77' are preferably made from a polymeric foam, preferably an elastic polymeric foam. Separating air ducts from one another may also be achieved by spacer material that is compressed at specific locations or by spacer material that has a variable density, or where different locations of the multi-zone mattress style support certain spacer material with different densities, the lower density spacer material forming the air ducts. A plurality of electrical resistance wires 78, 78', 78", 78'" is arranged on top of the plurality of air ducts 76, 76', 76" and separating walls 77, 77'. An additional layer 71, preferably made of an elastic polymer foam, is arranged on top of the plurality of electrical resistance wires 78, 78', 78", 78'", the plurality of air ducts 76, 76', 76" and the separating walls 77, 77'. The top layer 71 may be covered with an additional layer, for example, a layer made of a woven textile.

Upon heating, the warmth generated by the electrical resistance wires 78, 78', 78", 78'" due to being subjected to an electrical current will pass through layer 71 and warm up the bed environment there above. For cooling, the electrical resistance wires are not provided with electricity, and ambient air is forced to flow through the air ducts 76, 76', 76". The lower temperature of the ambient air in the air ducts 76, 76', 76" will cool down layer 71 and subsequently the bed environment there above.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measures cannot be used to advantage. Any reference signs in the claims should not be construed as limiting the scope.

The invention claimed is:

1. A system for adjusting the microclimate of a bed environment, the system comprising:
    multi-zone mattress-style support including a plurality of individual heating zones;
    means for heating the plurality of individual heating zones;
    means for cooling the multi-zone mattress-style support; and
    a plurality of temperature sensors, and
    wherein the means for cooling the multi-zone mattress-style support comprises at least one air duct, within the multi-zone mattress-style support, for transporting ambient air through the multi-zone mattress-style support, the at least one air duct comprising at least one inlet opening for receiving air and at least one outlet opening for output of the air,
    wherein the at least one air duct includes a plurality of longitudinally extending air ducts adjacent to each other and parallel to a longitudinal axis of the multi-zone mattress-style support, the adjacent air ducts being configured to transport air in opposite directions, and each of the adjacent air ducts having respective inlet and outlet openings of the at least one inlet opening and the at least one outlet opening, and
    wherein the at least one inlet opening of the at least one air duct is at a first side end of the at least one air duct for receiving the air along a longitudinal direction parallel to the longitudinal axis, and the at least one outlet opening of the at least one air duct is at a second side end of the at least one air duct for output of the air along the longitudinal direction, the first side end and the second side end being at opposite side ends of the at least one air duct.

2. The system according to claim 1, wherein the plurality of individual heating zones is configured to be heated individually.

3. The system according to claim 1, wherein the means for cooling further comprises at least one lowering means for lowering the air temperature below the temperature of the ambient air, said lowering means being selected from the group consisting of Peltier elements and cooling compressor units.

4. The system according to claim 1, wherein the means for cooling the multi-zone mattress-style support does not comprise any means for cooling the air to a temperature which is lower than the temperature of the ambient air.

5. The system according to claim 1, wherein each heating zone of the plurality of individual heating zones is provided with at least one temperature sensor of the plurality of temperature sensors.

6. The system according to claim 4, further comprising at least one additional temperature sensor for sensing the temperature of a room where the system is located.

7. The system according to 1, further comprising a controller operatively connected with the temperature sensors, the means for heating the plurality of individual heating zones, and the means for cooling the multi-zone mattress-style support.

8. The system according to 1, wherein the multi-zone mattress-style support is a mattress positionable directly on a slatted frame or a box spring, or is a topper mattress that can be laid on top of a mattress.

9. The system according to claim 1, wherein the at least one air duct comprises a plurality of air ducts with outlet openings arranged facing an upper face of the multi-zone mattress-style support.

10. The system according claim 1, wherein the at least one air duct comprises a plurality of air ducts with outlet openings, the outlet openings being arranged to a side of the multi-zone mattress-style support for preventing air to enter the bed and creating an air flow in a plane of the multi-zone mattress-style support.

11. The system according to claim 1, wherein the least one air duct includes a plurality of air ducts configured to provide individual zones that can be cooled independently of one another.

12. Use of a system as defined in claim 1 for adjusting the microclimate of a bed environment.

13. A method for adjusting the microclimate of a bed environment, the method comprising acts of:
measuring temperature of the bed environment in individual zones; and
adjusting the temperature of the bed environment in the individual zones such that the temperature in said individual zones is kept at a preset temperature,
wherein the adjusting act includes an act of warming by a heater or cooling by a cooler the individual zones to the preset temperature, the cooler having at least one air duct comprising at least one inlet opening and at least one outlet opening,
wherein the warming act includes an act of subjecting at least one electrical resistance wire in each individual heating zone of a multi-zone mattress-style support to an electric current thereby becoming warm, wherein the warmth is conducted from the electrical resistance to an upper face of the multi-zone mattress-style support by conduction,
wherein the cooling act includes an act of forcing air to flow through the at least one air duct within the multi-zone mattress-style support,
wherein the at least one air duct includes a plurality of air ducts adjacent to each other and parallel to a longitudinal axis of the multi-zone mattress-style support, the adjacent air ducts being configured to transport air in opposite directions, and each of the adjacent air ducts having respective inlet and outlet openings of the at least one inlet opening and the at least one outlet opening, and
wherein the at least one inlet opening of the at least one air duct of the respective inlet and outlet openings is at a first side end of the air duct for receiving the air along a longitudinal direction parallel to the longitudinal axis, and the at least one outlet opening of the at least one air duct is at a second side end of the at least one air duct for output of the air along the longitudinal direction, the first side end and the second side end being at opposite side ends of the at least one air duct.

14. The method according to claim 13, wherein temperature of the at least one air that is forced through the at least one air duct within the multi-zone mattress-style support is not lowered below temperature of ambient air.

15. The method according to claim 13, wherein temperature of the air that is forced through the at least one air duct within the multi-zone mattress-style support is lowered below temperature of ambient air.

16. A system for adjusting the microclimate of a bed environment, the system comprising:
a multi-zone mattress-style support including a plurality of individual heating zones;
a heater configured to heat the individual heating zones;
a cooler configured to cool the multi-zone mattress-style support; and
a plurality of temperature sensors,
wherein the cooler comprises at least one air duct, within the multi-zone mattress-style support, for transporting ambient air through the multi-zone mattress-style support, the at least one air duct comprising at least one inlet opening for receiving air and at least one outlet opening for output of air to the multi-zone mattress-style support,
wherein the at least one air duct includes a plurality of air ducts adjacent to each other and parallel to a longitudinal axis of the multi-zone mattress-style support, the adjacent air ducts being configured to transport air in opposite directions, and each of the adjacent air ducts having respective inlet and outlet opening of the at least one inlet opening and the at least one outlet opening, and
wherein the at least one inlet opening of the at least one air duct is at a first side end of the at least one air duct for receiving the air along a longitudinal direction parallel to the longitudinal axis, and the at least one outlet opening of the at least one air duct is at a second side end of the at least one air duct for output of the air along the longitudinal direction, the first end and the second end being at opposite side ends of the at least one air duct.

17. The method according to claim 13, wherein the at least one electrical resistance wire in each individual heating zone is a heating yarn integrated in a woven textile.

18. The system according to claim 16, wherein the heater is configured as a plurality of heating yarns integrated in a woven textile.

19. The system according to claim 16, further comprising:
an ambient air temperature sensor configured to measure an ambient air temperature of a sleeping room including the bed environment; and
a controller operatively connected with the ambient air temperature sensor, the plurality of temperature sensors, the heater and the cooler, the controller being configured to adjust the heater and the cooler at least based on the ambient air temperature measured by the ambient air temperature sensor.

* * * * *